(12) United States Patent
Shalaby

(10) Patent No.: US 8,057,817 B2
(45) Date of Patent: Nov. 15, 2011

(54) INTRAVAGINAL RINGED MESH DEVICE AND APPLICATOR THEREFOR

(75) Inventor: Shalaby W Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 970 days.

(21) Appl. No.: 11/667,933

(22) PCT Filed: Dec. 14, 2005

(86) PCT No.: PCT/US2005/045190
§ 371 (c)(1),
(2), (4) Date: May 16, 2007

(87) PCT Pub. No.: WO2006/065873
PCT Pub. Date: Jun. 22, 2006

(65) Prior Publication Data
US 2010/0062039 A1    Mar. 11, 2010

(51) Int. Cl.
*A61F 13/02* (2006.01)

(52) U.S. Cl. .......................................................... 424/433
(58) Field of Classification Search ........................ None
See application file for complete search history.

(56) References Cited

U.S. PATENT DOCUMENTS

2005/0175665 A1 *   8/2005   Hunter et al. ................. 424/423

* cited by examiner

*Primary Examiner* — Carlos Azpuru
(74) *Attorney, Agent, or Firm* — McCormick, Paulding & Huber LLP

(57) ABSTRACT

This invention generally covers a ringed-mesh intravaginal device and applicator therefore wherein the ringed-mesh comprises a composite ring comprising a flexible matrix containing one or more bioactive agent or agents and needed excipients or modulators, and the said matrix is reinforced with a fibrous construct to provided needed initial and in-use biomechanical stability. Of special application of the medicated, ringed-mesh is its use for securing contraception relying on biomechanical, pharmacological, and biochemical means.

19 Claims, No Drawings

INTRAVAGINAL RINGED MESH DEVICE AND APPLICATOR THEREFOR

FIELD OF THE INVENTION

This invention deals with an intravaginal, controlled drug release, ringed mesh device with multiple structural and compositional features to secure its intended functional performance. For mechanical stability at the vaginal site, the ring component of the device is a fiber-reinforced composite of an elastomeric silicone. To facilitate placement and minimize tissue trauma in the vagina, the device is affixed in a folded configuration to an applicator. To maximize device resilience and minimize contact area within the vaginal wall, the rim of the composite ring is designed to have a teardrop-shaped cross-sectional area with the narrow component of the teardrop interfacing with the vaginal wall and the broad component at the inside perimeter of the ring. For the specific application of the device for securing contraception, the composite ring is designed to encircle a mesh with tailored porosity and preferably surface charge to prevent the sperm diffusion through mesh and deflect it away from the surface, respectively.

BACKGROUND OF THE INVENTION

Prior applications of the same inventor have dealt with a fiber-reinforced composite ring for the controlled release of at least one bioactive agent incorporated in a biocompatible matrix reinforced with absorbable/biodegradable fibers capable of providing the mechanical properties needed for inserting and maintaining the ring in a body cavity for a desired period of time. Such ring system can be used for the intravaginal, intraperitoneal, and subcutaneous delivery of at least one bioactive agent, including those used as contraceptives.

U.S. application Ser. No. 10/860,677 discloses a controlled drug release device comprising a partially or fully absorbable, fiber-reinforced composite ring system comprising an absorbable or non-absorbable matrix, an absorbable, reinforcing fibrous construct and an absorbable coating to provide three modes of controlling the release of bioactive agents and one mode for modulating the mechanical property of the ring in a body cavity during device functional use. For partially absorbable ring systems, the drug release is dependent initially on the diffusion rate of the drug through the matrix and the absorbable coating. As the latter degrades with time, the diffusion through the matrix prevails. Meanwhile, as the absorbable fibrous reinforcing construct undergoes degradation with time, the mechanical strength of the composite ring decreases to provide the desired mechanical strength retention profile. For a fully absorbable composite ring system, the degradation of the matrix offers an additional mode of controlling the release profile as compared with the partially absorbable counterpart. In effect, the invention of U.S. application Ser. No. 10/860,677 deals with a fiber-reinforced composite ring system for the controlled release of at least one bioactive agent comprising a biocompatible matrix reinforced with an absorbable/biodegradable fibrous construct capable of providing the mechanical properties needed for inserting and maintaining said ring in a body cavity for the desired period of time, and wherein the absorbable/biodegradable reinforcing fibers are made primarily from one or more cyclic monomer(s) including glycolide, l-lactide, ϵ-caprolactone, p-dioxanone, and trimethylene carbonate.

For the partially absorbable/biodegradable composite ring controlled drug delivery system of U.S. Application No. 60/482,898, the fiber-reinforced composite ring deals with the controlled release of at least one bioactive agent and comprises a biocompatible matrix reinforced with absorbable/biodegradable fibers capable of providing the mechanical properties needed for inserting and maintaining said ring in a body cavity for the desired period of time, wherein the reinforcing fibers are absorbable/biodegradable and the matrix is non-absorbable/non-biodegradable, wherein the non-absorbable matrix comprising a methacrylate polymer derived from at least one alkyl methacrylate monomer, and wherein the methacrylate polymer is derived from one or more alkyl methacrylate monomer(s) and N-vinyl pyrrolidone. Alternatively, the matrix may comprise a cyclodextrin or cyclodextrin derivative.

Obviously, the partially absorbable/biodegradable composite ring controlled drug delivery system of U.S. application Ser. No. 10/860,677 did not fully address the use of matrices such as silicones and polyether urethanes, which are cited in the prior art as safe carriers of many bioactive agents.

Accordingly, a CIP for U.S. application Ser. No. 10/935,808 was filed on Sep. 8, 2004, and dealt with a partially absorbable, fiber-reinforced composite for the controlled delivery of at least one bioactive agent comprising an absorbable fiber construct capable of providing time-dependent mechanical properties of a biostable elastomeric copolymeric matrix containing an absorbable microparticulate ion-exchanging polymer to modulate the release of said bioactive agent for the desired period of time at a specific biological site, wherein (1) the absorbable reinforcing fibers are formed from at least one cyclic monomer selected from the group consisting of glycolide, l-lactide, ϵ-caprolactone, p-dioxanone, trimethylene carbonate, and a morpholine-2,5-dione; and (2) the biostable matrix is made of a polyether urethane elastomer or a silicone elastomer, such as copolymer polysiloxane, comprising dimethyl siloxane sequences, which can be made of at least one of the Silastic® family of silicone elastomers.

Obviously, the previous applications and related teachings did not disclose (1) the use of a non-absorbable reinforcing construct in the composite ring; (2) a novel cross-sectional geometry of the ring and associated clinical benefits in terms of ease of placement and minimized vaginal tissue trauma; (3) use of a novel feature entailing the presence of a mesh encircled by the composite ring, wherein such mesh can be used as a spermiostatic net in a contraceptive device and/or a depot for the release of bioactive agents including antimicrobials and antivirals; and (4) a ring applicator that can be used as needed by the patient without physician intervention.

SUMMARY OF THE INVENTION

Accordingly, the present invention addresses these issues from a technical and clinical perspective.

Generally, the present invention is directed to an intravaginal device which is a ringed, flat mesh encircled with a fiber-reinforced composite ring, the composite ring providing for the controlled delivery of at least one bioactive agent, the ring being formed of a fibrous construct contained within a compliant, elastomeric copolymeric matrix, the fibrous construct providing adequate stiffness and resilience for in-use biomechanical stability, the copolymeric matrix further containing solid excipients to modulate the pH about the ring and the concentration of the at least one bioactive agent.

More specifically, the present invention is directed to an intravaginal device comprising a ringed, flat mesh encircled with a fiber-reinforced composite ring for the controlled delivery of at least one bioactive agent wherein said ring comprising a fibrous construct that is capable of imparting needed stiffness, resilience, and in-use biomechanical stability to a compliant elastomeric copolymeric matrix thereof containing solid excipients to modulate the pH of the aqueous eluates and concentration of the bioactive agent or agents released therein, wherein said mesh is a biostable, non-woven, melt-blown, porous polyolefin fabric, such as those made o polyethylene or polypropylene, having an average pore diameter of less than 100 microns and preferably less than 20 microns and more preferably less than 7 microns and the encircling ring is made of a crosslinked silicone elastomeric copolymer reinforced with a circular band of high-melting multifilament yarn sized with a low-melting polymer.

In a specific situation, the flat fabric mesh is made of melt-blown fabric comprising polypropylene microdenier fibers and the fiber-reinforced composite ring comprising a crosslinked silicone elastomer reinforced with polyethylene terephthalate multifilament band sized with poly-ϵ-caprolactone wherein the said matrix contains ferrous gluconate or ferrous ascorbate as a spermiostatic/spermicidal agent and at lease one excipient selected from the group represented by ascorbic acid, carboxyl-bearing polyglycolide, glycine, citric acid, oxalic acid, tartaric acid, and glycolic acid. Because of its composition and design, the intravaginal device is conceived as a multifaceted, biomechanically, biochemically, and pharmacologically active device for securing contraception in humans and animals. A key feature of such device and particularly the flat mesh is that the polypropylene fibers of the mesh are surface sulfonated to repel approaching, negatively charged sperms. This is associated with the fact that the sperms have a negatively charged surface that will be repelled by the negatively charged sulfonate-bearing surface of the mesh. This and the limited porosity of the mesh, which can be associated with a pore diameter of less than 7 microns, will prevent the sperm diffusion through the mesh as the sperm has a head diameter of about 7 microns. Another key feature of the polyolefin or more specifically polypropylene flat mesh is that its fibers may contain an antimicrobial agent or agents such as triclosan.

Another specific aspect of this invention deals with an intravaginal device comprising a ringed, flat mesh encircled with a fiber-reinforced composite ring for the controlled delivery of at least one bioactive agent wherein said ring comprising a fibrous construct that is capable of imparting needed stiffness, resilience, and in-use biomechanical stability to a compliant elastomeric copolymeric matrix thereof containing solid excipients to modulate the pH of the aqueous eluates and concentration of the bioactive agent or agents released therein, wherein said mesh is a knitted or woven fabric or an electrostatically spun non-woven fabric comprising microfibers having an average diameter of less than 6 microns, and having an average pore diameter of less than 100 microns and preferably less than 20 microns, and more preferably less than 10 and most preferably less than 7 microns and the encircling ring is made of a crosslinked silicone elastomer reinforced with a circular band of high-melting, multifilament yarn sized with a low-melting polymer, wherein the fabric mesh comprising a slow-absorbing, multifilament yarn of segmented lactide copolymer and the fiber-reinforced composite ring comprising a crosslinked silicon elastomer reinforced with segmented lactide-copolymeric multifilament yarn sized with a linear or triaxial 95/5 caprolactone/glycolide copolymer wherein the said matrix contains ferrous gluconate or ferrous ascorbate as a spermicidal agent and at least one excipient selected from the group represented by ascorbic acid, carboxyl-bearing polyglycolide, glycine, citric acid, oxalic acid, tartaric acid, and glycolic acid. Accordingly, such ringed mesh is viewed as being multifaceted, biomechanically, biochemically, and pharmacologically active for securing contraception in humans and animals. Additional key features of this ringed, knitted, woven or electrospun non-woven mesh are associated with the provisions that (1) the lactide-copolymeric fibers of the flat mesh are surface pretreated with a dilute alkaline solution to yield high concentrations of negative charge to repel any approaching negatively charged sperms; (2) the lactide-copolymeric fibers of the flat mesh contains a slow-releasing antimicrobial agent or agents such as triclosan; (3) the lactide-copolymeric fibers of the flat mesh is coated with an antiviral or antimicrobial-containing polymer; and (4) the microfibers of the electrospun non-woven fabric contain ferrous gluconate or a mixture of ferrous gluconate and ascorbic acid.

Further, the present invention is directed to an intravaginal ring applicator which is formed of a tubular component capable of housing a flexible intravaginal ring device in a folded or curled configuration and means for displacing the ring from the tubular component upon insertion into the vaginal cavity, such that upon displacement from the tubular component the flexible ring device opens into an essentially flat configuration. An alternative form of the application entails a flexible tube with two holes at one end through which is threaded a thin filament. The latter is used to hold a folded configuration of the ring during insertion. At the site of application, the filament is withdrawn to allow the ring to unfold and acquire its normal shape across the vaginal canal.

DETAILED DESCRIPTION OF PREFERRED EMBODIMENTS

This invention deals with an intravaginal controlled drug delivery device comprising a ringed mesh encircled with a composite ring. The mesh can be made of (1) non-absorbable, non-woven, melt-blown polyolefin fabric, which is, in turn, made of polyethylene or polypropylene; (2) a woven or knitted fabric which is, in turn, made of a polyester (e.g., polyethylene terephthalate or segmented polybutylene terephthalate-polyether copolymer) or polyamide (e.g., Nylon 6, Nylon 66, Nylon 610, and Nylon 11); (3) a non-woven, electrospun microfabric, which is, in turn, made of a segmented lactide copolymer; and/or (4) a woven or knitted fabric, which is, in turn, made of a segmented lactide copolymer. The fibers constituting the mesh may contain one or more antimicrobial agent or agents (e.g., triclosan, miconazole, metronidazole) and/or antiviral agent. The mesh porosity may be associated with a pore diameter of less than 500 microns or as small as being less than 7 microns. The mesh porosity may be further controlled by applying a surface coating which preferably contains antimicrobial and/or antiviral agents. Having such controllably low porosity and particularly one that is associated with a pore diameter of less than 7 microns will prevent the passage to the uterus of sperms having an average head diameter of about 7 microns. Accordingly, the ringed mesh secures contraception through its designed biomechanical and barrier properties. For uncoated meshes, the surface can be chemically treated to develop a dense negative charge on the surface of the mesh, which is capable of repelling approaching negatively charged sperms. The negative surface charge can be developed by (1) sulfonating or maleating (following by hydrolysis) meshes made of a polyolefin or a non-absorbable polyester; or (2) treating the surface of absorbable meshes with dilute alkaline solution to produce anion-forming carboxylic groups. The mesh and the encircling ring may contain a similar or dissimilar colorant for improved aesthetics and visual recognition.

The composite encircling ring can be virtually non-absorbable wherein the matrix is made of crosslinked silicone elastomer reinforced with a band of sized, non-absorbable multifilament yarn. The sized yarn can be made of polyethylene terephthalate multifilament yarn, which is sized by a low melting, virtually non-absorbable coating or sizing agent, such as polycaprolactone, polybutylene adipate, or polyethylene adipate. In effect, the yarn is coated with the sizing agent to achieve an add-on of 10-30 percent. The coated yarn is then wound on a mandrel to form a coated, circular band. Heating the latter at or slightly above the melting temperature of the coating (or sizing agent) yields a band comprising multifilaments which are practically encased in the low melting coating. Attaching several bands to a mesh substrate can be achieved (1) by placing the bands on the mesh and heating them in the presence of light compressive force; or (2) by applying a light compressive force and activating the fusion of the sizing agent at the band/mesh interface, using microwave radiation. Individual ringed meshes are separated using an ultrasonic or laser cutting method. The fused band/mesh constructs are placed in the cavity of a heatable mold into which the curable silicone components containing the bioactive agents and needed excipients are injected. After heat curing, the mold is cooled, opened, and the individual ringed meshes are isolated. Surface activation of the mesh may precede its attachment to the sized band. However, surface coating can be applied on the mesh components of the assembled ringed mesh for reducing the pore diameter of the mesh.

For composite encircling rings which are partially absorbable, the (1) matrix can be made of a crosslinked silicone elastomer containing the bioactive agent and needed excipients; and (2) the reinforcing fibrous construct can be made from a segmented lactide copolymer in the form of multifilament yarn sized with a linear or triaxial caprolactone/glycolide copolymer. Assembling the partially absorbable ring with a slow-absorbing mesh made of segmented lactide copolymer can be achieved as described above for the virtually non-absorbable ringed mesh.

For ringed meshes intended for use to secure contraception in humans or animals, the composite ring may contain (1) ferrous gluconate and/or ferrous ascorbate—the latter can be used to prolong the release period of the ferrous ions simultaneously with the ascorbic acid, which may be advantageous over the well-established spermicidal ferrous gluconate; (2) acids (e.g., oxalic, citric, tartaric, malic, and glycolic acids) and/or acid producing polymers (e.g., carboxyl-bearing, low molecular polyglycolide) to help maintaining the vaginal pH below 6 and preferably at 3-4.5; (3) an amino acid (e.g., glycine) to help mediate the acidity of the initial eluates; (4) ascorbic acid or sodium ascorbate to interact with proteins of vaginal mucus and render them more viscous and hence, reducing the sperm motility; and (5) degradable cation-exchanger (e.g., carboxyl-bearing polyglycolide) to constantly regulate the diffusion of the ferrous ion, particularly during the early segment of the application period. Another important feature of the partially absorbable ringed mesh is the use of a slow-absorbing, reinforcing fibrous construct to insure immediate biomechanical stability of the ring following its placement and gradual increase in compliance through incremental degradation and strength loss toward the end of the use period, to minimize late mechanical discomfort. Additionally, as the construct degrades, the released acidic by-products will contribute to the role of the acid-producing excipients.

In all cases, the ringed meshes can be sterilized by traditional methods or at least disinfected using a combination of isopropyl alcohol and UV radiation, without compromising their functional performance.

To facilitate the use of the intravaginal ringed mesh, or for that matter, any composite intravaginal controlled release system, this invention deals with a patient-friendly applicator comprising a polymeric tabular component and a string. In a typical design, the ring or ringed mesh is folded in an elongated configuration and placed inside the distal end of the tubular component of the applicator and above the knot of two interlaced, coated, braided threads (or strings) with the four ends extending upward to thread through four holes near the distal rim of the tubular component and revert downward to and beyond the proximal end outside such tube. During insertion, braided threads of the loaded applicator remain stationary. Following the insertion, the patient can pull out the thread while withdrawing the tube. The simultaneous pulling of the thread and withdrawal of the tube result in a synchronized extrusion and unfolding of the ring or the ringed mesh with the removal of the tubular component of the applicator. The tubular component can be made by injection molding of a flexible thermoplastic polymer, such as low-density polyethylene or polycaprolactone. The braided thread can be Made of absorbable (e.g., segmented lactide copolymer) or non-absorbable (e.g., Nylon 66) multifilament yarn. The braided string or thread can be coated with a linear or polyaxial absorbable (95/5 caprolactone/glycolide copolymer) or non-absorbable, lubricious, low-molecular weight, low-melting material to facilitate its inward and outward passage during the placement of the intravaginal device.

Alternatively, a plunger may be employed to displace the ring into the vaginal cavity.

Although the teaching of this invention addresses in more detail the contraceptive ringed mesh system, the use of the designs and compositions covered by the invention for other applications is by no means precluded. In effect, the composite ringed meshes, or just the composite rings and applicators therefor, can be used for the treatment and/or prevention of vaginal infection by anaerobic or aerobic bacteria, fungi, and/or viruses. They also can be used in treating cervical cancer.

In certain applications, the composite ring may be coated with an absorbable or non-absorbable coating in order to modulate the release of its active ingredients and needed excipients.

In concert with the aforementioned teaching, it is obvious that this invention deals with an intravaginal, controlled drug release, ringed mesh device with multiple structural and compositional features to secure its intended functional performance. For mechanical stability at the vaginal site, the ring component of the device is a fiber-reinforced composite of an elastomeric silicone. To facilitate placement and minimize tissue trauma in the vagina, the device is affixed in a folded configuration to an applicator. To maximize device resilience and minimize contact area within the vaginal wall, the rim of the composite ring is designed to have a teardrop-shaped cross-sectional area with the narrow component of the teardrop interfacing with the vaginal wall and the broad component at the inside perimeter of the ring. For the specific application of the device for securing contraception, the composite ring is designed to encircle a mesh with tailored porosity and preferably surface charge to prevent the sperm diffusion through mesh and deflect it away from the surface, respectively.

To emphasize the broad scope of this invention and its teaching, it is to be noted that it deals generally with an intravaginal device comprising a ringed, flat mesh encircled with a fiber-reinforced composite ring for the controlled delivery of at least one bioactive agent wherein said ring comprising a fibrous construct that is capable of imparting needed stiffness, resilience, and in-use biomechanical stability to a compliant elastomeric copolymeric matrix thereof containing solid excipients to modulate the pH of the aqueous eluates and concentration of the bioactive agent or agents released therein, wherein said mesh is a biostable, non-woven, melt-blown, porous polyolefin fabric, such as those made o polyethylene or polypropylene, having an average pore diameter of less than 100 microns and preferably less than 20 microns and more preferably less than 7 microns and the encircling ring is made of a crosslinked silicone elastomeric copolymer reinforced with a circular band of high-melting multifilament yarn sized with a low-melting polymer.

In a specific situation, the flat fabric mesh is made of melt-blown fabric comprising polypropylene microdenier fibers and the fiber-reinforced composite ring comprising a crosslinked silicone elastomer reinforced with polyethylene terephthalate multifilament band sized with poly-c-caprolactone wherein the said matrix contains ferrous gluconate or ferrous ascorbate as a spermiostatic/spermicidal agent and at lease one excipient selected from the group represented by ascorbic acid, carboxyl-bearing polyglycolide, glycine, citric acid, oxalic acid, tartaric acid, and glycolic acid. Because of its composition and design, the intravaginal device is conceived as a multifaceted, biomechanically, biochemically, and pharmacologically active device for securing contraception in humans and animals. A key feature of such device and particularly the flat mesh is that the polypropylene fibers of the mesh are surface sulfonated to repel approaching, negatively charged sperms. This is associated with the fact that the sperms have a negatively charged surface that will be repelled by the negatively charged sulfonate-bearing surface of the mesh. This and the limited porosity of the mesh, which can be associated with a pore diameter of less than 7 microns, will prevent the sperm diffusion through the mesh as the sperm has a head diameter of about 7 microns. Another key feature of the polyolefin or more specifically polypropylene flat mesh is that its fibers may contain an antimicrobial agent or agents such as Triclosan.

Another specific aspect of this invention deals with an intravaginal device comprising a ringed, flat mesh encircled with a fiber-reinforced composite ring for the controlled delivery of at least one bioactive agent wherein said ring comprising a fibrous construct that is capable of imparting needed stiffness, resilience, and in-use biomechanical stability to a compliant elastomeric copolymeric matrix thereof containing solid excipients to modulate the pH of the aqueous eluates and concentration of the bioactive agent or agents released therein, wherein said mesh is a knitted or woven fabric or electrostatically spun non-woven fabric comprising microfibers having an average diameter of less than 6 microns, and having an average pore diameter of less than 100 microns and preferably less than 20 microns, and more preferably less than 10 and most preferably less than 7 microns and the encircling ring is made of a crosslinked silicone elastomer reinforced with a circular band of high-melting, multifilament yarn sized with a low-melting polymer, wherein the fabric mesh comprising a slow-absorbing, multifilament yarn of segmented lactide copolymer and the fiber-reinforced composite ring comprising a crosslinked silicon elastomer reinforced with segmented lactide-copolymeric multifilament yarn sized with a linear or triaxial 95/5 caprolactone/glycolide copolymer wherein the said matrix contains ferrous gluconate or ferrous ascorbate as a spermicidal agent and at least one excipient selected from the group represented by ascorbic acid, carboxyl-bearing polyglycolide, glycine, citric acid, oxalic acid, tartaric acid, and glycolic acid. Accordingly, such ringed mesh is viewed as being multifaceted, biomechanically, biochemically, and pharmacologically active for securing contraception in humans and animals. Additional key features of this ringed, knitted, or woven mesh are associated with the provisions that (1) the lactide-copolymeric fibers of the flat mesh are surface pretreated with a dilute alkaline solution to yield high concentrations of negative charge to repel any approaching negatively charged sperms; (2) the lactide-copolymeric fibers of the flat mesh contains a slow-releasing antimicrobial agent or agents such as triclosan; (3) the lactide-copolymeric fibers of the flat mesh is coated with an antiviral or antimicrobial-containing polymer; and (4) the microfibers of the electrospun non-woven fabric contain ferrous gluconate or a mixture of ferrous gluconate and ascorbic acid.

This invention also deals with an intravaginal ring applicator comprising a tubular component for placing a folded configuration of the said ring and a string for retaining the ring configuration during placement at the vaginal site and subsequent unfolding to acquire a circular configuration thereat. An alternative form of the application entails a flexible tube with two holes at one end through which is threaded thin filament. The latter is used to hold a folded configuration of the ring during insertion. At the site of application, the filament is withdrawn to allow the ring to unfold and acquire its normal shape across the vaginal canal.

Further illustrations of the present invention are provided by the following examples:

Example 1

Preparation of Acid-terminated Polyglycolide Cation-Exchanging Microparticulate (PG-61)

Glycolide was polymerized in the presence of glycolic acid and stannous octanoate to produce low molecular weight, hydrolytically degradable polyester PG-61, as described in U.S. Pat. No. 6,413,539. Purification and reduction in size of PG-61 was also conducted as per U.S. Pat. No. 6,413,539 teaching.

Example 2

Preparation of Linear 95/5 ε-Caprolactone/Glycolide Copolymer Coating (CT-1)

The CT-1 copolymer was prepared by the copolymerization of ε-caprolactone (0.625 mole) with glycolide (32.3 mmole) in the presence of glycolic acid (3.756 mmole) as the initiator and stannous octanoate (0.1247 mmole as 0.2M solution in toluene) as the catalyst. The polymerization was conducted in a mechanically stirred reactor under a dry nitrogen atmosphere at 150° C. for 6.25 hours. At the conclusion of the polymerization, as determined by GPC, traces of unreacted monomer were removed by distillation under reduced pressure. The composition of the purified polymer was verified by IR and NMR. The polymer was shown to melt at 55° C. as determined by DSC.

Example 3

Preparation of Triaxial 95/5 ε-Caprolactone/Glycolide Copolymer Coating (CT-2)

The CT-1 copolymer was prepared by the copolymerization of c-caprolactone (0.625 mole) with glycolide (32.3 mmole) in the presence of triethanolamine (1.05 mmole) as the initiator and stannous octanoate (0.1247 mmole as 0.2M solution in toluene) as the catalyst. The polymerization was conducted in a mechanically stirred reactor under a dry nitrogen atmosphere at 150° C. for 8.0 hours. At the conclusion of the polymerization, as determined by GPC, traces of unreacted monomer were removed by distillation under reduced pressure. The composition of the purified polymer was verified by IR and NMR. The polymer was shown to melt at 61° C. as determined by DSC.

Example 4

Preparation of Segmented 88/12 l-Lactide/Trimethylene Carbonate Copolymer (S-P) and It's Conversions to Multifilament Yarn (S-Y)

The copolymer S-P was prepared, purified and characterized following the general procedures described in U.S. Pat. No. 6,342,065 (2002) associated with segmented l-lactide copolymers of similar compositions. The polymer was melt spun and oriented as per the general procedure descried in U.S. Pat. No. 6,342,065. More specifically (1) a single ¾" screw extruder equipped with a melt pump and 25-hole die was used; and (2) for spin-drawing, a series of heated and unheated godets were used in line with the extruder to achieve the desired single filament diameter and total yarn denier.

Example 5

Preparation of Sized Yarn (SS-Y) and Processing into Circular Bands

General Method

The multifilament yarn (S-Y) from example 4 was plied into a multiplet of eight, 25-filament yarn, annealed at 80° C. for 30 minutes under tension. The plied yarn is then threaded through a 10-20 percent acetone solution of coating polymer, CT-2, and dried in line. The dried, coated yarn (with 15-30 percent add-on) is wound on a special mandrel to form several circular bands (for use as reinforcing fibrous constructs in the composite ring). The mandrel is heated for more than 5 minutes in an oven maintained at 80±2° C. to allow the coating to bind the multifilament yarn into coherent bands.

Example 6

Knitting of Multifilament Yarn (S-Y)

Multifilament yarn, S-Y, from example 4 is used with or without plying into higher denier yarn to knit into meshes with an average pore diameter of less than 500 microns. The meshes are annealed under tension at 80±2° C. for 30 minutes to stabilize their dimensions. The porosity of the mesh is determined, in terms of coverage pore diameter, using optical microscopy.

Example 7

Electrostatic Spinning of Segmented 88/12 l-Lactide/Trimethylene Carbonate Copolymer (S-P) and Formation of Non-Woven Fabric

General Method

A 7-9 percent solution of S-P (from Example 4) in an 80/20 solution of $CHCl_3/CH_2Cl_2$ was electrospun into non-woven fabric of about 0.2-0.7 mm in thickness comprising microfibers having an average diameter of less than 6 microns. The electrospinning was conducted under the following conditions using a 60 mL syringe with stainless steel, 20-gauge flat needle, and a stainless steel drum as positive and grounding electrodes, respectively: voltage, 15-20 kV; flow rate, 0.05 to 0.10 mL/min. The non-woven fabric was dried on the drum and removed for use.

Example 8

Affixing the Circular Bands on the Flat Meshes from Example 6

General Method

Individual flat meshes from example 6 are anchored on a Teflon sheet and the meshes are marked to designate the locations for placing and fusing the circular bands. The bands are then placed on the marked locations and the band/mesh interfaces are formed by placing a second sheet of Teflon on the bands and heating at 80±2° C. for less than one minute. The assembled mesh/bands are cut and readied for use in insert molding as described in example 9.

Example 9

Assembling and Testing of a Partially Absorbable, Ringed Mesh

General Method

Listed below are the components of an active matrix that are mixed and introduced into a closed, 2-part Teflon mold having a ring-type cavity with teardrop-shaped cross-section (overall OD=55 mm; ID=47.5 mm; ring volume=348 $mm^3$; surface area=2371 $mm^3$; teardrop cross-section horizontal width=7.5 mm; internal curved wide end corresponding to a radius of 2.5 mm; external curved narrow end corresponding to a radius of 2 mm), an inlet for introducing the reactants, and an Outlet to exit displaced dry nitrogen used in pre-purging the dry mold. The lower half of the mold is designed to have a shallow few-micron crater to accommodate the mesh component of the mesh/band (M/B) assembly (from example 8). The M/B assembly from example 7 is placed into the lower half of the mold cavity. A fraction of the components listed below, which have been mixed under nitrogen, is charged into the lower half of the open mold containing the multifilament band with adherent component of the mesh under a nitrogen atmosphere. The top part is then placed on the lower part, and the mold is closed and mechanically secured. The remaining fraction of the mixed components is then injected into the mold through the feed port after purging with nitrogen.

List of Mixed Matrix Components and Filler

Two-component Silastic®
Fibrous Construct (sized multifilament band with adherent component of the mesh)
Microparticulate Cation-exchanger (from Example 1)
Bioactive agent(s)

The charged mold is heated at 80° C. for the required period of time. At the conclusion of the heating cycle, the ringed mesh is removed and coated, if so needed, with 95/5 poly (caprolactone-co-glycolide)(from Example 2) by dipping in a 5 percent acetone solution. After drying, the ringed mesh is then used for testing in a phosphate buffered solution at 37° C.

as a function of time for: (1) the drug release profile at Ph 4.5; and (2) compressibility retention profile, as measured in terms of the radial deformation force (RDF) that is required to attain a predetermined degree of deformation, using an MTS Universal Tester (858 MiniBionix) in the compression mode.

Example 10

Assembling a Typical Partially Absorbable Ringed Mesh for Contraceptive Application The ringed mesh is assembled as described in the general method of example 9 using the following active ingredients and excipients as part of the matrix composition. The curing is conducted at 80° C. for 4 hours.

| Silastic Matrix ® | |
| --- | --- |
| Type | Q7-4840 |
| Weight of Component A, g | 2.3 |
| Weight of Component B, g | 2.3 |
| Fibrous Construct$^a$, mg | ~185 |
| Active Ingredient, mg | |
| Ferrous Gluconate | 380 |
| Excipient | |
| Ascorbic Acid, mg | 340 |
| Cation-exchanger$^b$, mg | 160 |
| Glycine$^c$, mg | 40 |

$^a$Sized multifilament (about 150 mg yarn + 25 mg sizing agent + ~10 mg adherent mesh component)
$^b$Cation-exchanger/acid precursor such as PG-61 from example 1.
$^c$As pH modulator Example 11

Coating the Exposed Part of the Mesh in Ringed/Mesh Assembly

General Method

This is conducted to reduce the pore diameter if so desired. Accordingly, the composite ring part is placed behind a mask and acetone solution (5-10 percent) of coating polymer CT-2 (from example 3) is applied onto the mesh using a microspray gun (or nebulizer). At the conclusion of the coating process, the ringed mesh is placed in a laminar flow hood at 25° C. and then under reduced pressure to remove residual solvent.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An intravaginal device comprising a ringed, flat mesh encircled with a fiber-reinforced composite ring, the composite ring providing for the controlled delivery of at least one bioactive agent, the ring comprising a fibrous construct contained within a compliant, elastomeric copolymeric matrix, the fibrous construct providing adequate stiffness and resilience for in-use biomechanical stability, the copolymeric matrix further containing solid excipients to modulate the pH about the ring and the concentration of the at least one bioactive agent.

2. An intravaginal device as set forth in claim 1 wherein the mesh is a biostable, non-woven, melt-blown, porous polyolefin fabric having an average pore diameter of less than 100 microns, wherein the copolymeric matrix of the composite ring comprises a crosslinked silicone elastomeric copolymer, and wherein the reinforcing, fibrous construct comprises a circular band of high-melting multifilament yarn sized with a low-melting polymer.

3. An intravaginal device as set forth in claim 2 wherein the melt-blown polyolefin fabric comprises polypropylene microdenier fibers, wherein the copolymeric matrix contains ferrous gluconate as a spermiostatic/spermicidal agent and at least one excipient selected from the group consisting of ascorbic acid, carboxyl-bearing polyglycolide, glycine, citric acid, oxalic acid, tartaric acid, and glycolic acid, and wherein the reinforcing, fibrous construct comprises a polyethylene terephthalate multifilament band sized with poly-ε-caprolactone 4. An intravaginal device as set forth in claim 3 as a multifaceted, biomechanically, biochemically, and pharmacologically active device for securing contraception in humans and animals.

5. An intravaginal device as set forth in claim 3 wherein the polypropylene fibers of the flat mesh are surface sulfonated to repel approaching, negatively charged sperms.

6. An intravaginal device as set forth in claim 3 wherein the polypropylene fibers of the flat mesh contain at least one slow-releasing antimicrobial agent.

7. An intravaginal device as set forth in claim 3 wherein the flat mesh is coated with an antimicrobial-containing polymer.

8. An intravaginal device as set forth in claim 1 wherein the mesh comprises a knitted fabric having an average pore diameter of less than 100 microns, wherein the copolymeric matrix of the composite ring comprises a crosslinked silicone elastomer, and wherein the reinforcing, fibrous construct comprises a circular band of high-melting, multifilament yarn sized with a low-melting polymer.

9. An intravaginal device as set forth in claim 8 wherein the knitted fabric of the mesh comprises a slow-absorbing, multifilament yarn of segmented lactide copolymer, wherein the copolymeric matrix contains ferrous gluconate as a spermicidal agent and at least one excipient selected from the group consisting of ascorbic acid, carboxyl-bearing polyglycolide, glycine, citric acid, oxalic acid, tartaric acid, and glycolic acid, and wherein the reinforcing, fibrous ring comprises a segmented lactide-copolymeric multifilament band sized with a triaxial 95/5 caprolactone/glycolide copolymer.

10. An intravaginal device as set forth in claim 9 as a multifaceted, biomechanically, biochemically, and pharmacologically active for securing contraception in humans and animals.

11. An intravaginal device as in claim 10 wherein the lactide-copolymeric fibers of the flat mesh are surface pretreated with a dilute alkaline solution for yielding a high concentration of negative charge to repel approaching negatively-charged sperms.

12. An intravaginal device as set forth in claim 9 wherein the lactide-copolymeric fibers of the flat mesh contain at least one slow-releasing antimicrobial agent.

13. An intravaginal device as set forth in claim 9 wherein the lactide-copolymeric fibers of the flat mesh are coated with an antimicrobial-containing polymer.

14. An intravaginal device as set forth in claim 1 wherein the mesh comprises a woven fabric having an average pore diameter of less than 100 microns, wherein the copolymeric matrix of the composite ring comprises a crosslinked silicone elastomer and wherein the reinforcing, fibrous construct of the composite ring comprises a circular band of high-melting, multifilament yarn sized with a low-melting polymer.

15. An intravaginal device as set forth in claim 14 wherein the woven fabric comprises a slow-absorbing, multifilament yarn of segmented lactide copolymer, wherein the copolymeric matrix contains ferrous gluconate as a spermicidal agent and at least one excipient selected from the group consisting of ascorbic acid, carboxyl-bearing polyglycolide, glycine, citric acid, oxalic acid, tartaric acid, and glycolic acid, and wherein reinforcing fibrous construct comprises a segmented lactide-copolymeric multifilament band sized with a triaxial 95/5 caprolactone/glycolide copolymer.

16. An intravaginal device as set forth in claim 15 as a multifaceted, biomechanically, biochemically, and pharmacologically active for securing contraception in humans and animals.

17. An intravaginal device as set forth in claim 15 wherein the lactide-copolymeric fibers of the flat mesh are surface pretreated with a dilute alkaline solution for yielding a high concentration of negative charge to repel approaching negatively-charged sperms.

18. An intravaginal device as set forth in claim 15 wherein the lactide-copolymeric fibers of the flat mesh contain at least one slow-releasing antimicrobial agent.

19. An intravaginal device as set forth in claim 15 wherein the lactide-copolymeric fibers of the flat mesh are coated with an antimicrobial-containing polymer.

\* \* \* \* \*